US012702338B2

(12) United States Patent
Lee et al.

(10) Patent No.: US 12,702,338 B2
(45) Date of Patent: Aug. 11, 2026

(54) FABRICS CONFORMALLY COATED WITH CONJUGATED POLYMERS, DISPOSABLE HEALTH MONITORING SENSORS USING THE SAME, AND FABRICATION METHOD THEREOF

(71) Applicant: Purdue Research Foundation, West Lafayette, IN (US)

(72) Inventors: Sunghwan Lee, West Lafayette, IN (US); Hyeonghun Kim, Icheon-si (KR); Michael Vincent Clevenger, English, IN (US); Jung Joo Sohn, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 855 days.

(21) Appl. No.: 17/843,570

(22) Filed: Jun. 17, 2022

(65) Prior Publication Data

US 2022/0401002 A1 Dec. 22, 2022

Related U.S. Application Data

(60) Provisional application No. 63/211,982, filed on Jun. 17, 2021.

(51) Int. Cl.
*A61B 5/27* (2021.01)
*A61B 5/00* (2006.01)
*A61B 5/021* (2006.01)
*A61B 5/024* (2006.01)
(Continued)

(52) U.S. Cl.
CPC ................ *A61B 5/27* (2021.01); *A61B 5/021* (2013.01); *A61B 5/0816* (2013.01); *A61B 5/268* (2021.01); *A61B 5/6803* (2013.01); *A61B 5/6806* (2013.01); *A61B 5/024* (2013.01)

(58) Field of Classification Search
None
See application file for complete search history.

(56) References Cited

U.S. PATENT DOCUMENTS

2016/0310032 A1* 10/2016 Sotzing ................ A61B 5/6804
2018/0005766 A1* 1/2018 Fairbanks ............. H10K 30/81
(Continued)

OTHER PUBLICATIONS

Liu et al. (Flexible, Stretchable Sensors for Wearable Health Monitoring: Sensing Mechanisms, Materials, Fabrication Strategies and Features; Sensors 2018, 18, 645; doi:10.3390/s18020645). (Year: 2018).*

(Continued)

*Primary Examiner* — Jay B Shah
(74) *Attorney, Agent, or Firm* — Purdue Research Foundation

(57) ABSTRACT

A wearable device may include a sensor. The sensor may include a flexible fabric, a conjugated polymer coating deposited on the fabric via vapor-phase oxidative chemical vapor deposition (oCVD), and a plurality of electrodes in coupled to the conjugated polymer coating. The wearable device may further include a processor communicatively coupled to the electrodes. The processor may measure an electrical property across the electrodes, determine a physiological event based on the measured electrical property, and output measurement information corresponding the physiological event.

15 Claims, 13 Drawing Sheets

(51) Int. Cl.
*A61B 5/08* (2006.01)
*A61B 5/268* (2021.01)

(56) References Cited

U.S. PATENT DOCUMENTS

2018/0325420 A1* 11/2018 Gigi ..................... A61B 5/6823
2018/0340847 A1* 11/2018 Pan ........................ A41D 1/002

OTHER PUBLICATIONS

Zhao, P. et al., Strain-discriminable pressure/proximity sensing of transparent stretchable electronic skin based on PEDOT:PSS/SWCNT electrodes. ACS Appl. Mater. Interfaces 12, 55083-55093 (2020).
Li, Z. et al., Gelatin methacryloyl-based tactile sensors for medical wearables. Adv. Funct. Mater. 30, 2003601 (2020).
Chen, T. et al., Highly sensitive and wide-detection range pressure sensor constructed on a hierarchical-structured conductive fabric as a human-machine interface. Nanoscale 12, 21271-21279 (2020).
Lee, J.J. et al., Alcohol-based highly conductive polymer for conformal nanocoatings on hydrophobic surfaces toward a highly sensitive and stable pressure sensor. NPG Asia Mater. 12, 65 (2020).
Tseng, Y.-T. et al., Morphology and properties of PEDOT:PSS/soft polymer blends through hydrogen bonding interaction and their pressure sensor application. J. Mater. Chem. C 8, 6013-6024 (2020).
Sun, L. et al., Realization of flexible pressure sensor based on conductive polymer composite via using electrical impedance tomography. Smart Mater. Struct. 29, 055004 (2020).
Li, Y. et al., Extending the pressure sensing range of porous polypyrrole with multiscale microstructures. Nanoscale 12, 2081-2088 (2020).
Wang, J.-C. et al., Miniaturized flexible piezoresistive pressure sensors: poly(3,4-ethylenedioxythiophene):poly (styrenesulfonate) copolymers blended with graphene oxide for biomedical applications. ACS Appl. Mater. Interfaces 11, 34305-34315 (2019).
Wang, Z. et al. Flexible and washable poly(ionic liquid) nanofibrous membrane with moisture proof pressure sensing for real-life wearable electronics. ACS Appl. Mater. Interfaces 11, 27200-27209 (2019).
Nichols, W.W., Clinical measurement of arterial stiffness obtained from noninvasive pressure waveforms. Am. J. Hypertens. 18, 3S-10S (2005).
Park, J. et al., Tailoring force sensitivity and selectivity by microstructure engineering of multidirectional electronic skins. NPG Asia Mater. 10, 163-176 (2018).
Dagdeviren, C. et al., Conformable amplified lead zirconate titanate sensors with enhanced piezoelectric response for cutaneous pressure monitoring. Nat. Commun. 5, 4496 (2014).

* cited by examiner

FABRICS CONFORMALLY COATED WITH CONJUGATED POLYMERS, DISPOSABLE HEALTH MONITORING SENSORS USING THE SAME, AND FABRICATION METHOD THEREOF

CROSS REFERENCE TO RELATED APPLICATIONS

This application claims the benefit of U.S. Provisional Application No. 63/211,982 filed Jun. 17, 2021, the entirety of which is herein incorporated by reference.

TECHNICAL FIELD

This disclosure relates to sensors and, in particular, to wearable sensors.

BRIEF DESCRIPTION OF THE DRAWINGS

The embodiments may be better understood with reference to the following drawings and description. The components in the figures are not necessarily to scale. Moreover, in the figures, like-referenced numerals designate corresponding parts throughout the different views.

DETAILED DESCRIPTION

Figure 1:
FIG. 1 Illustrates an example of a system for physiological measurement using a conjugated polymer coated sensor.
Figure 1:
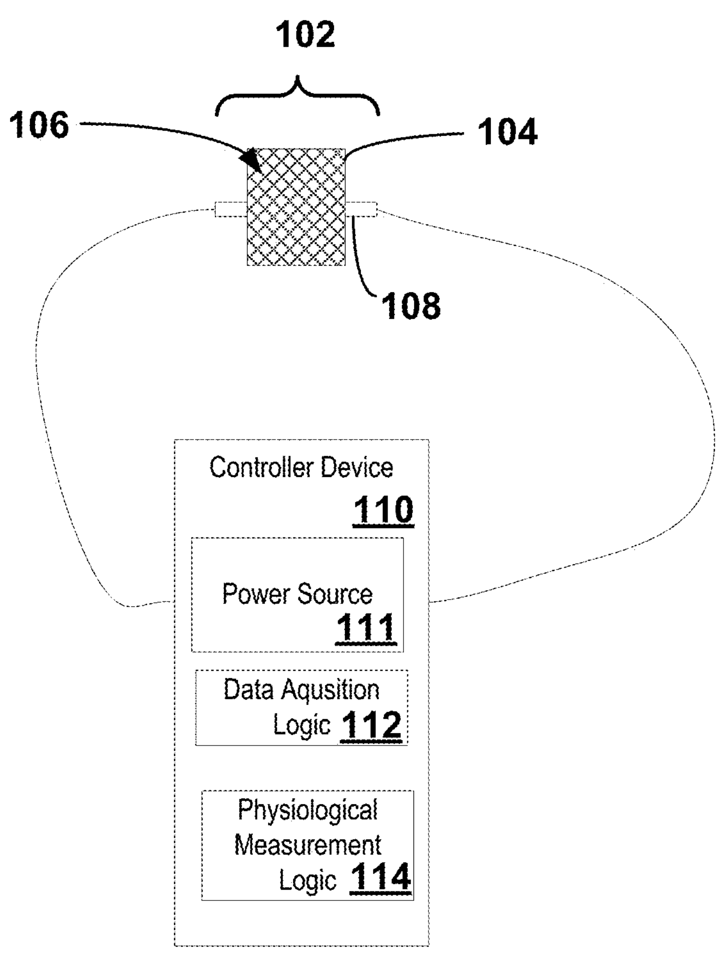

Wearable sensors may provide sensing important bio-information such as body temperature, blood pressure, or respiratory patterns from the human body without the aid of medical experts. While the development of these sensory devices are specifically tailored and specialized depending on which types of bio information is being analyzed, or where the intended location of the sensor is being placed, flexibility and robustness is needed to provide the compatibility of the device on any location of a living body and the prolonged service despite undergoing the mechanical stress and strain caused by daily motion.

In an effort to provide flexibility, elastomers such as polyimide, polydimethylsiloxane, or fabrics have been adopted as device substrates. Among them, fabrics have shown tremendous advantages in remarkable stability, skin compatibility, breathability, and in being lightweight. Moreover, if a sensor is able to be directly fabricated onto ready-made wearables, such as clothes, gloves, or disposable masks, one can monitor their health status with minimized inconvenience. However, owing to fabric's rough nature of the surface, high porosity, and surface hydrophobicity, the formation of a uniform sensing film on the fabric has been regarded as a daunting task compared to developing films on flat and rigid substrates. This issue is especially noticed when using solution-based conductive polymers, which are one of the most commonly utilized materials for wearable sensors, because the thin-film formation of the materials relies on a liquid-phase deposition technique and its processing requirements such as surface wetting. Solution-based techniques, such as in situ chemical polymerization, dip-coating, or drop-casting methods have been utilized for coating a polymeric film onto a fabric. However, these conventional methods have been limited due to the requirements of suitable surface-wettability and required chemical functional groups on the fabrics for binding liquid-phase monomers or dispersed polymers in a solvent. In addition, the harsh conditions required for the liquid-based methods, such as annealing processing temperatures higher than 150° C. or necessary acid-treatment, have become another factor limiting the types of candidates for sensor substrates. Furthermore, the usage of additives, such as binders, that are often used for improving conformability of versatile fabrics, ultimately failed to maintain the inherent advantages of the fabrics (e.g., breathability or skin compatibility), as well as ultimately lower the conductivity due to the insulating nature of the binder.

Oxidative chemical vapor deposition (oCVD) has recently emerged as an innovative and unique method for synthesizing conductive polymer films with superior conductivity. Functionally, the conductive polymer films are synthesized by through the polymerization of a vaporized monomer and oxidizing agent. The vapor-phase reagents uniformly coat the whole surface of any substance regardless of surface morphology and wetting properties, enabling highly uniform polymer layers on virtually any substrates. The outstanding step-coverage facilitated by the oCVD technique has been a breakthrough for a wide range of research fields such as light-emitting diodes, lithium-ion batteries, or redox-flow batteries, where oCVD polymers have been conformally coated on vertically aligned nanowires or porous media. However, for wearable sensors, there has been limited progress to date.

Herein, we utilize the oCVD technique for creating a conformal poly(3,4-ethylene dioxythiophene) (PEDOT) layer on multiple fabrics (nylon, polyester, and cotton). Such fabrics may be included on or integrated with wearables (i.e. gloves and masks) for sensory devices without any binders or additives. The oCVD technique is capable of creating a highly conductive PEDOT film where thickness is readily controllable from ~10 nm to thicker than 1 μm by varying the deposition time. Moreover, the mechanical stability, breathability, and lightness of fabrics are consistent even after the PEDOT coating, implying oCVD PEDOT is notably promising as an active material for potential wearable devices. Based on the unique properties associated with oCVD deposited PEDOT, the system and methods described herein provide resistive sensors by directly printing PEDOT on a fabric for various applications including, for example, extracting blood pressure information, respiratory rates, and/or other physiological measurements in real-time with remarkable precision.

FIG. 1 illustrates a first example of a system. The system may include a sensor 102. The sensor 102 may include a flexible fabric 104. The fabric 102 may be a material produced by weaving or knitting fibers. For example, the fabric 102 may be a piece of cloth fabric. Alternatively, the fabric 104 may be coupled to an article of clothing. The fabric 104 may be coated in a conjugated polymer 106. The conjugated polymer 106 may be deposited on the fabric 104 via vapor-phase oxidative chemical vapor deposition (oCVD). The sensor 100 may further include a plurality of electrodes 108 coupled to the conjugated polymer coating.

The system may further include a controller device 110. The controller device may include a power source 111. The power source 111 may include circuitry that provides power across the electrodes. In some examples, the power source may include a battery. The power source 111 may apply power accords the electrodes. Electrical properties, such as voltage, current, and/or conductivity may be measured across the electrodes 108. The controller device may further include data acquisition logic 112 and/or physiological measurement logic 114.

Figure 2:
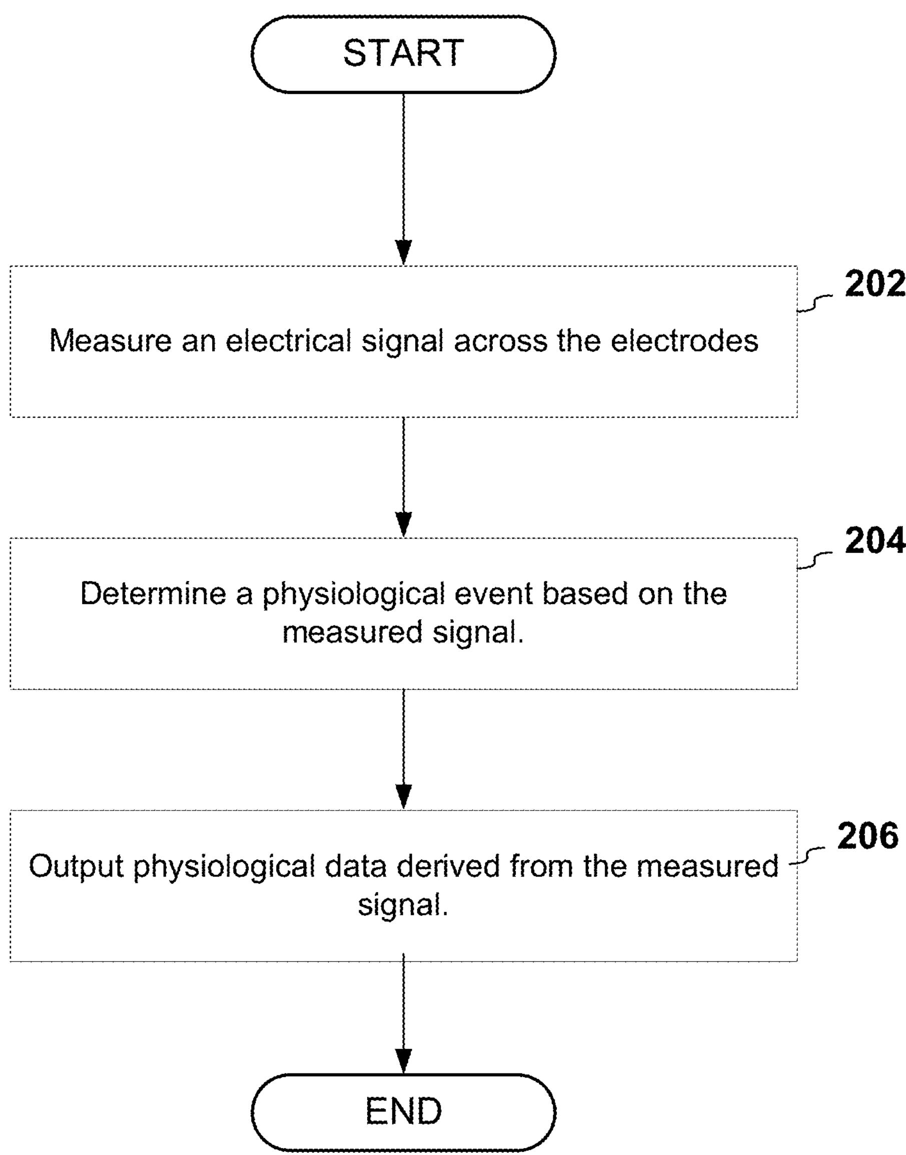
FIG. 2 illustrates an example flow diagram for logic of the system 100.

FIG. 2 illustrates an example flow diagram for logic of the system 100. Reference to FIG. 1 is made throughout the following discussion of FIG. 2. The data acquisition logic 112 may measure an electrical signal across the electrodes 108 (or the fabric 104 directly) (202). For example, the controller device 110 may connect to the electrodes 108 and/or fabric 104 via lead wires. The data acquisition logic 112 may measure an electrical signal(s) across the electrodes 112. For example, the data acquisition logic 112 may generate measurement information indicative of electrical properties, such as resistance, conductivity, current, etc.

The physiological measurement logic 114 may determine a physiological event based on the measured signal (204). For example, the physiological measurement logic 114 may detect a change in resistance, conductivity, etc. Alternatively, or in addition, the physiological measurement logic 114 may convert the electrical property measurement into a pressure measurement and detect a change in pressure measurement. In this case, if pressure (external stimulus in this case) is applied, the fabric is strained (or the dimensions are changed). Due to the change in the dimension, the resistance of the fabric changes. This means that if the pressure changes, the dimension changes, and therefore the recorded resistance (or current) changes. Therefore, the oCVD PEDOT-coated fabric can work as a pressure sensor since the current varies as a function of pressure. Once the sensor is calibrated by a reference relationship of current vs applied pressure, the sensor measures and calibrates the physical deformations to show how much pressure is applied.

The physiological measurement logic 114 may include logic that compares the derived pressure reading(s) with predefined pressure activity to determine the presence of a physiological event. The event could include, for example, inhalation, exhalation, pulse, etc. In some examples, the physiological measurement may be used to generate further physiological measurements including, for example, vitals, such as heart/pulse rate, blood pressure, and respiration rate.

The controller device 110 may output the physiological data derived from the measured signal (206). The physiological data may include information indicative of the physiological event. Alternatively or in addition, the physiological data may include the physiological measurements. Outputting the physiological data may include, communicating the physiological data over a wired or wireless interface, storing the physiological data in memory, and/or causing the physiological data to be displayed.

The system may be manifested in various examples and embodiments. In some examples, the sensor 102 and/or the controller device 100 may be included in a wearable device. Various examples of wearable devices are described below.

Figure 3:
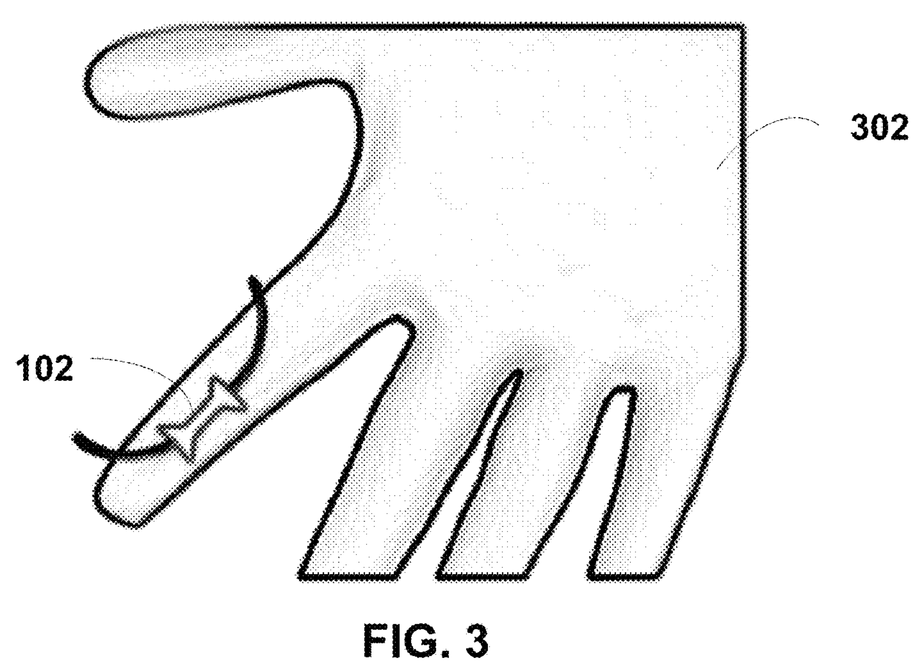
FIG. 3 illustrates an example of a wearable device including a sensor included on a glove.

FIG. 3 illustrates an example of a wearable device including the sensor 102 included on a glove 302. The sensor 102 may be attached or embedded in the glove 102. When the sensor is embedded, the fabric may be attached to or embedded on the glove. The movement of the fabric of the sensor 102 caused by pulse beats may cause changes in resistance, or some other electrical property, across the electrodes. The electrical property may be measured and converted into blood pressure and/or pulse rates. The output from the device may include pulse rate, blood pressure, etc.

Figure 4A:
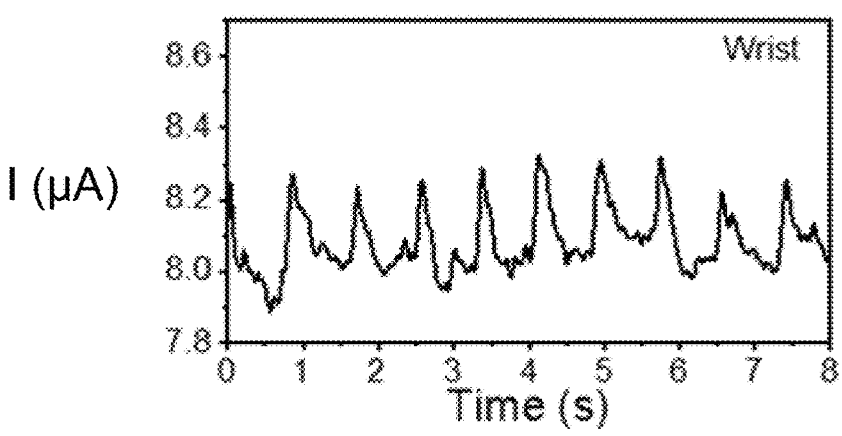
FIG. 4A-B illustrate examples of current vs time graphs for a sensor 102 being placed on various locations of a subject.
Figure 4B:
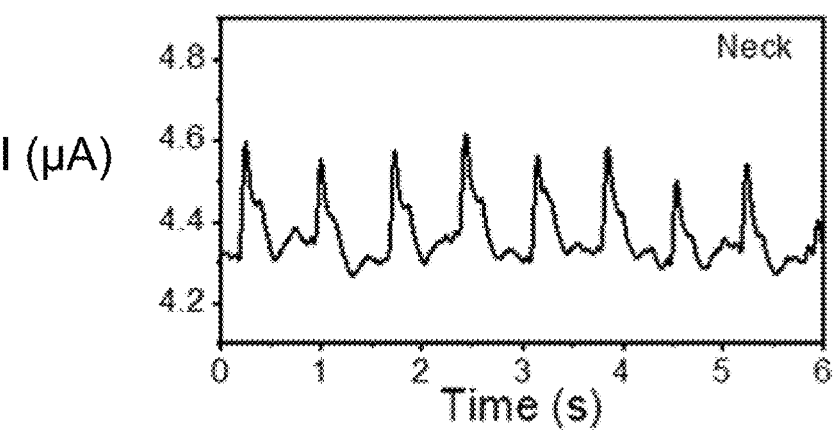

FIGS. 4A-B illustrate examples of current vs time graphs for the sensor 102 being placed on various locations of a subject. FIG. 4A illustrates an example of a current vs time graph of a human pulse when the glove sensor is pressed against a wrist. FIG. 4B. illustrates an example of a current vs time graph of a human pulse when the glove sensor is pressed against a neck artery. In both examples, a clear pulse rhythm may be detected which can be used to measure pulse or derive physiological measurements.

Figure 5:
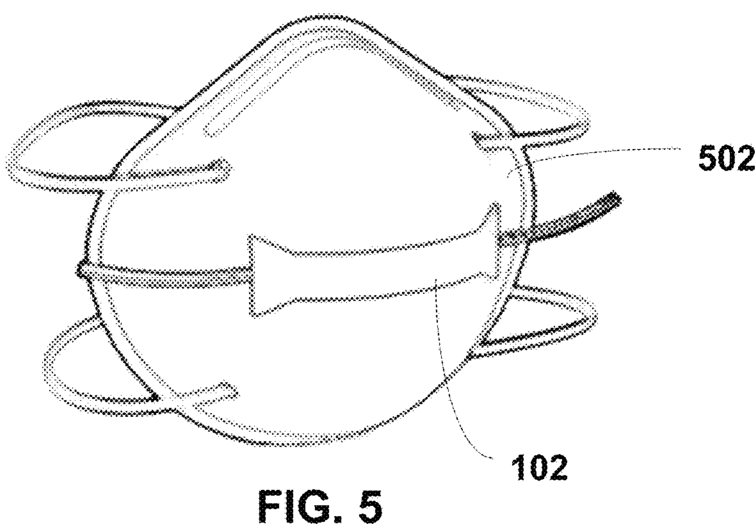
FIG. 5 illustrates an example of a wearable device including a fabric face mask and a sensor for measuring respiration.

FIG. 5 illustrates an example of a wearable device including a fabric face mask 502 and the sensor 102 for measuring respiration. The sensor 102 may be attached to or embedded in the face mask 502. When the sensor is embedded in the face mask 502, the fabric of the face mask 502 may receive the electrodes and the conjugated polymer deposition. Deformations of the face mask 502 caused by breathing may cause the resistance across the electrodes to change. The change in resistance and/or pressure may be categorized as a breathing event (i.e. breathing in/out). These inhalation and exhalation events may be compared with time to generate a respiratory rate. Output from the device may include the inhalation events, exhalation events, and/or the respiration rate.

Figure 6A:
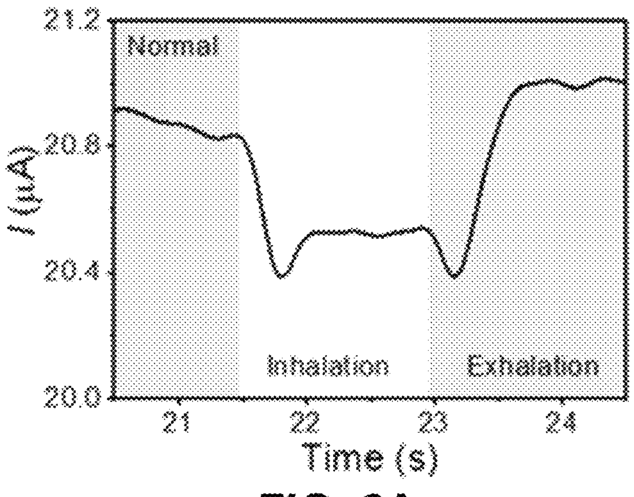
FIG. 6A-B illustrates an example measurements of human respiration as a function of sensor current vs time based on output from a sensor.
Figure 6B:
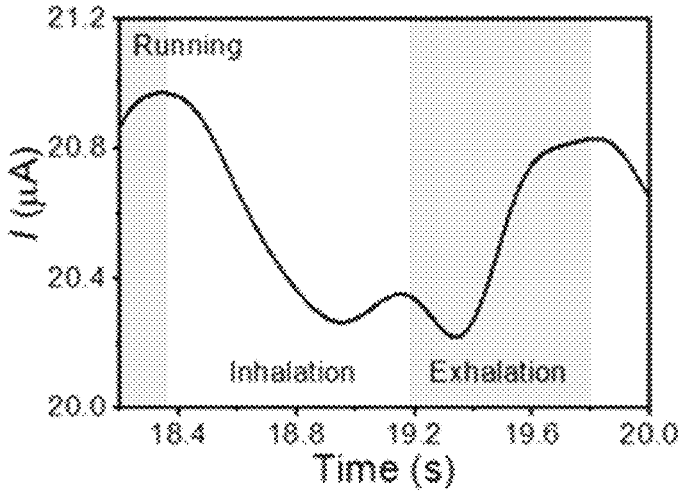

FIG. 6A-B illustrates an example measurement of human respiration as a function of sensor current vs time based on output from the sensor. FIG. 6A illustrates current vs time for normal respiration. FIG. 6B illustrates current vs time for respiration during exertion. In each of the figures, the electrical property (i.e. current) is measured over time. Changes in the electrical property over time are classified as "normal", "inhalation", and "exhalation". The processor may perform these classifications based on predefined thresholds, statistical relationships and/or machine learning models.

Figure 7:
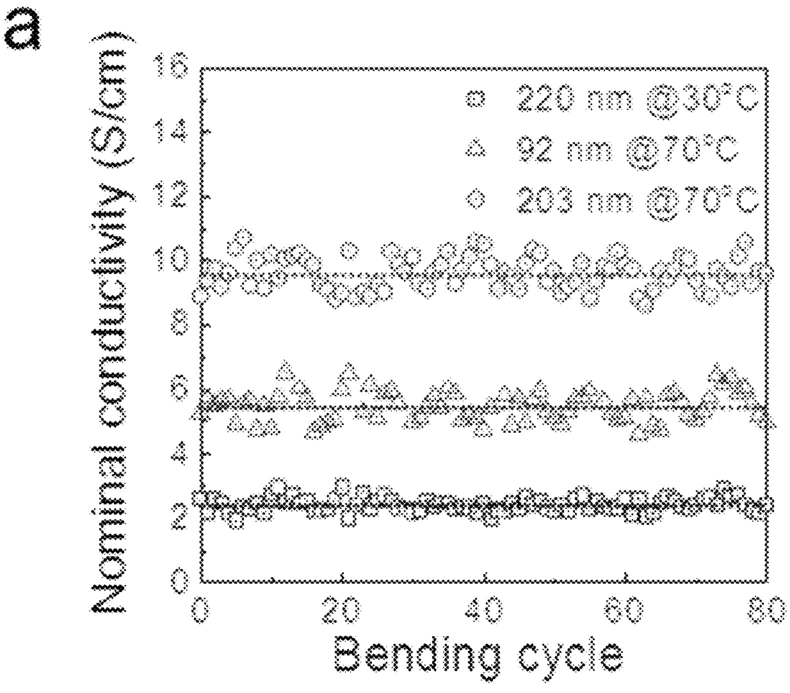
FIG. 7 illustrates an example of conductivity vs bending cycle plot of bending tests completed on conjugated polymer coated cotton fabrics.

FIG. 7 illustrates an example of conductivity vs bending cycle plot of bending tests completed on oCVD conjugated polymer (PEDOT) coated cotton fabrics. The oCVD conjugate polymers provide the ability to maintain their performance while undergoing bending cycles typical of what is experienced with standard wearables.

Figure 8:
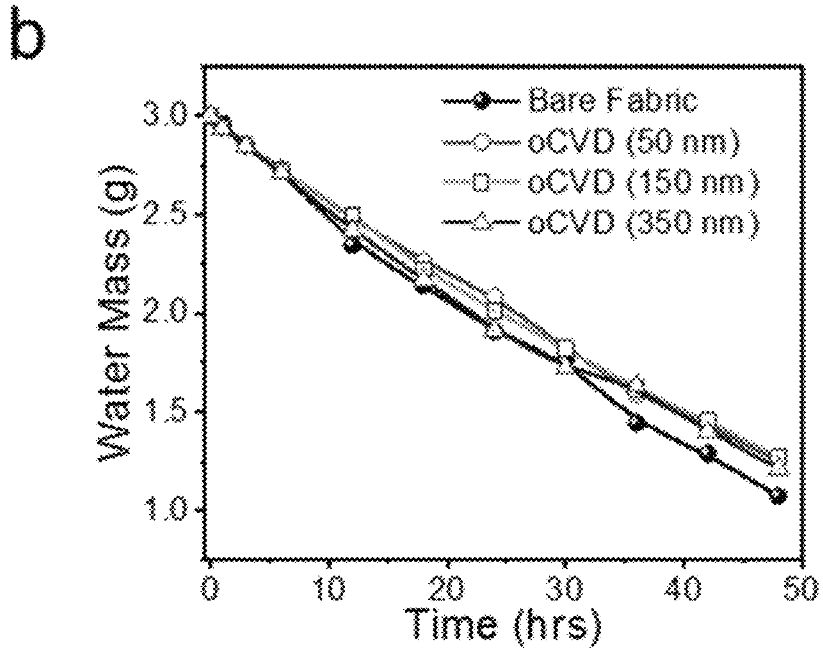
FIG. 8 illustrate breathability test comparing bare fabric to conjugated polymer coated cotton fabrics.

FIG. 8 illustrate breathability test comparing bare fabric to oCVD conjugated polymer (PEDOT) coated cotton fabrics. oCVD conjugated polymers provide excellent conformality by not substantially reducing breathability of fabrics despite being coated with a conjugated polymer.

Figures 9A, 9B, 9C:
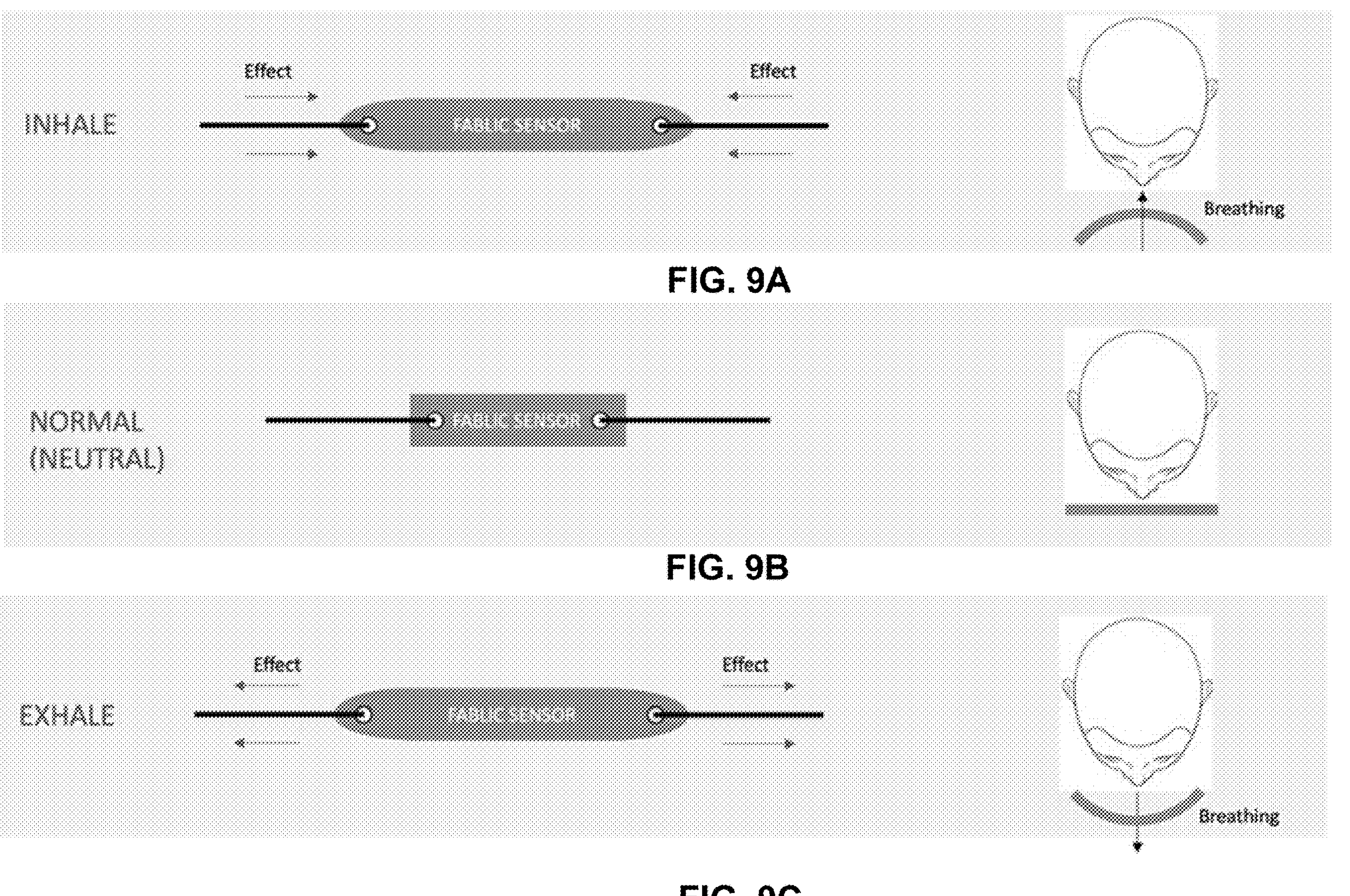
FIG. 9A-C illustrates an example of a sensor in various states for measuring respiration.

FIG. 9A-C illustrates an example of the sensor in various states for measuring respiration. Referring to FIG. 9A, the sensor may bend toward a user during inhalation. The fabric sensor is physically stretched by inhaling and exhaling when people breathe. So, the effect is that the sensor will be extended by air, and the arrow shows the direction of the force. Referring to FIG. 9B, the sensor may rest in a neutral position when air not in the process of being inhales or exhaled. FIG. 9C illustrates the sensor being bent away from the user during exhaling. When the fabric bends, this may cause changes in the fabric dimensions (or elongation) and hence the resistance of the fabric, which may be measured across the electrodes.

Figures 10A, 10B:
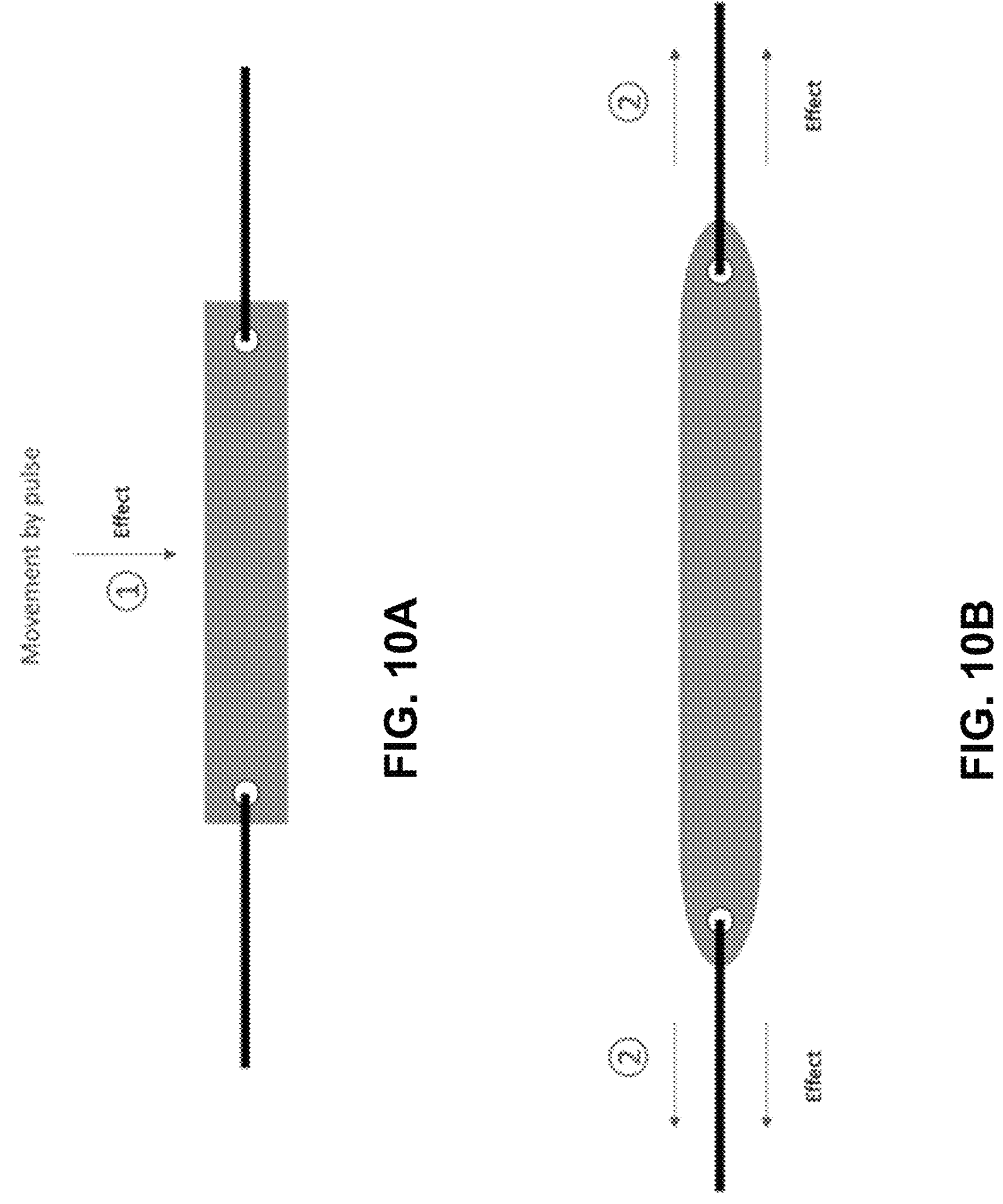
FIG. 10A-B illustrates an example of a sensor in various state for measuring pulse.

FIG. 10A-B illustrates an example of the sensor in various state for measuring pulse. FIG. 10A illustrates the sensor before a pulse causes movement. FIG. 10B illustrates the sensor during a pulse. The effect arrow in FIG. 10A shows a physical force from a pulse. The effect arrow in FIG. 10A which thereby causes the force shown by the effect arrow in FIG. 10B, wherein the fabric is stretched physically.

Figure 11:
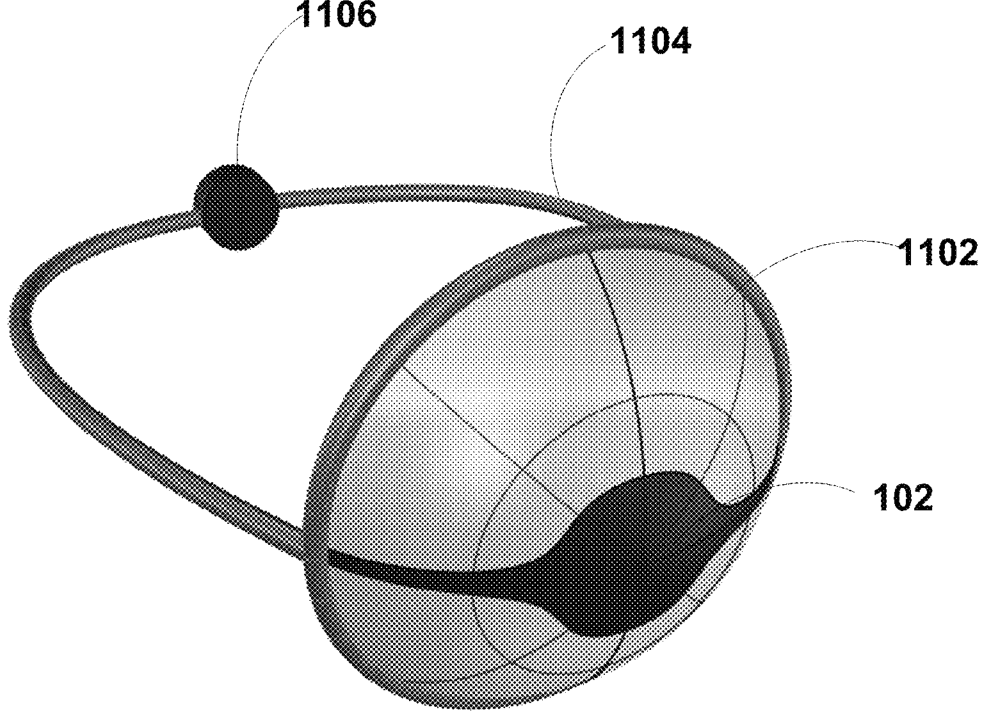
FIG. 11 illustrates a perspective view of a wearable device including a mask and a sensor, electric wires 1104, and a housing.

FIG. 11 illustrates a perspective view of a wearable device including a mask and the sensor 102, electric wires 1104, and a housing 1106. The housing 1106 may include the controller device 110 (see FIG. 1). In some examples, the sensor 102 may be embedded in the fabric of the mask 1102. The mask may be large enough to cover the mouth and nose.

Figures 12A, 12B:
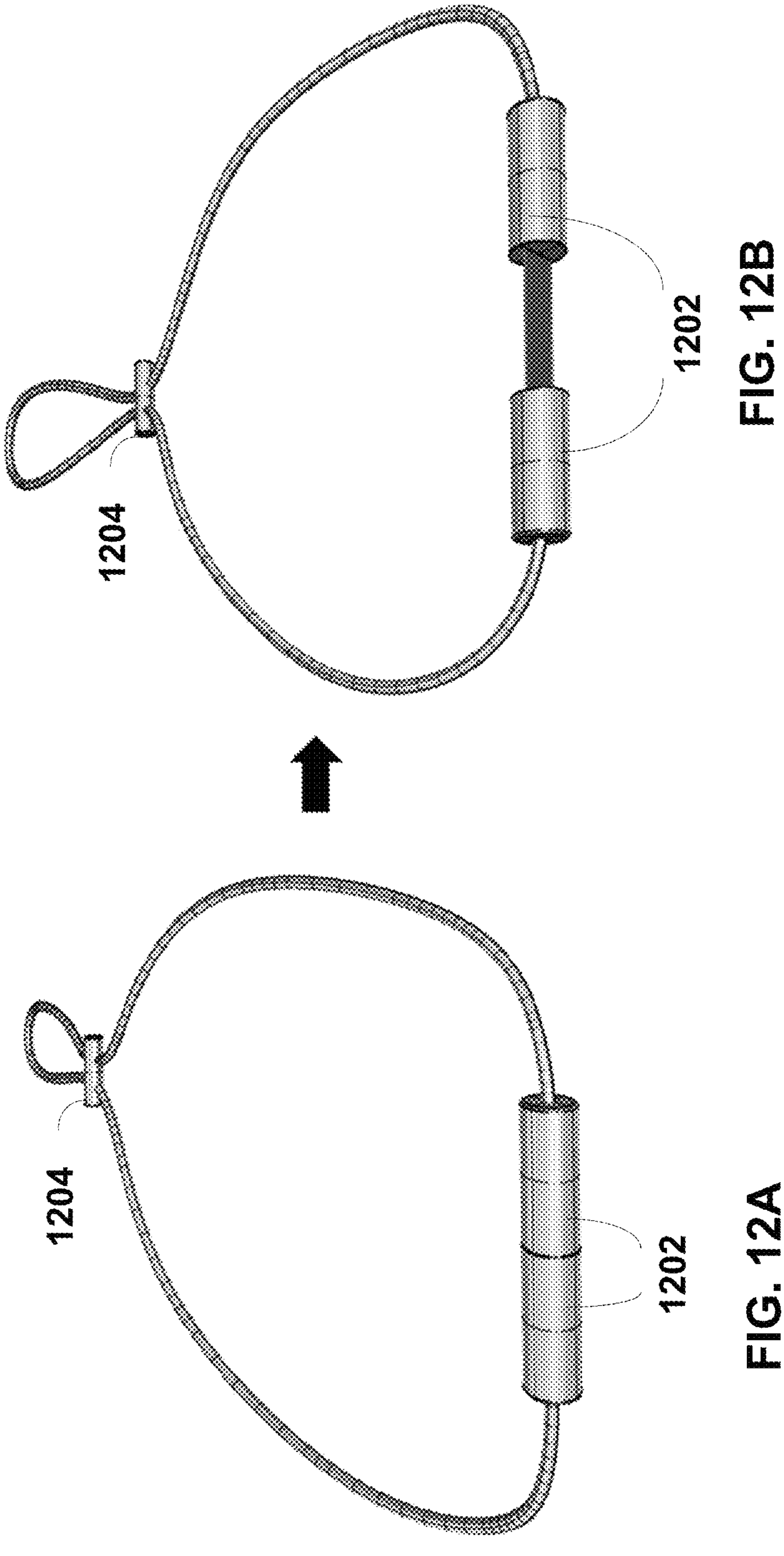
FIG. 12A-B illustrates perspective view of a non-obstructive mask having a sensor.

FIG. 12A-B illustrates perspective view of a non-obstructive mask having the sensor. In this example the mask may be positioned in front of the nose, leaving a substantially unobstructed path for breathing. The sensor may be in the form of a strip. The device may include a band which wraps around the head of a subject and attaches to the subject. The band may include electric wires which connect to a controller positioned in a housing. The housing may also include a tensioner for the band to adjust the tightness of the bands on the subject.

The mask may further include movable one or more movable covers 1202 which move or expand to expose the sensor. FIG. 12A illustrates the covers in a closed position. FIG. 12B illustrates the covers in an opened position. The band may extend through the covers such that the band supports the in the expanded state. In some examples, there may be two covers which magnetically clasp together with magnets included in the covers.

Figure 13:
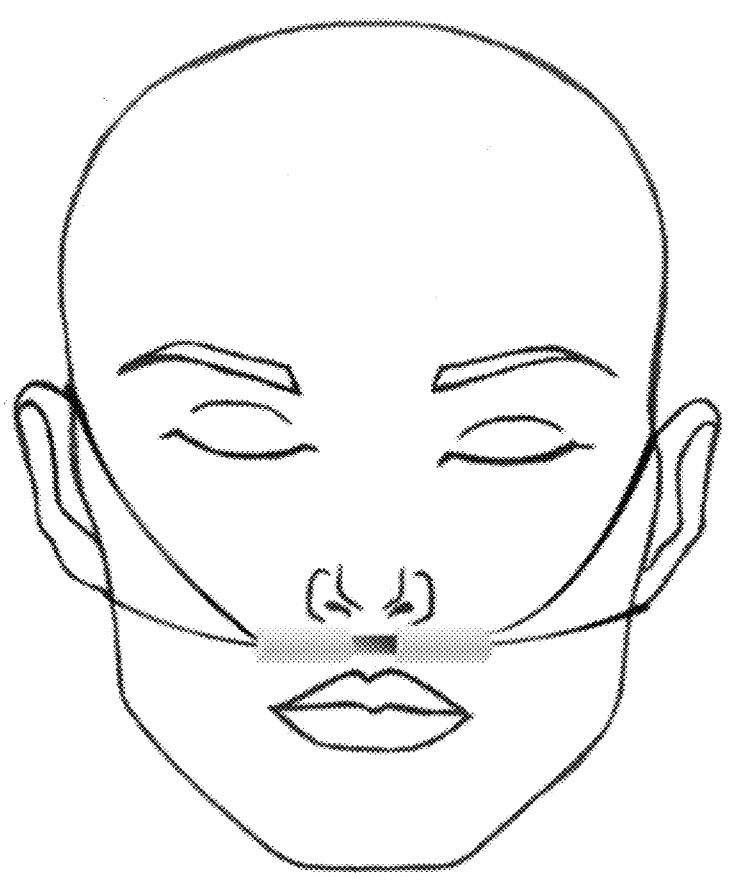
FIG. 13. illustrates an example of a non-obstructive mask positioned on a subject.

FIG. 13 illustrates an example of the non-obstructive mask positioned on a subject. As illustrated in FIG. 13, the mask may not obstruct the mouth of a subject and minimally obstruct the nose to allow for easy breathing.

As described herein, the term subject refers to any human or non-human mammal. Accordingly, the head illustrated in FIG. 13 may be replaced with a non-human head, such as a dog.

Figure 14:
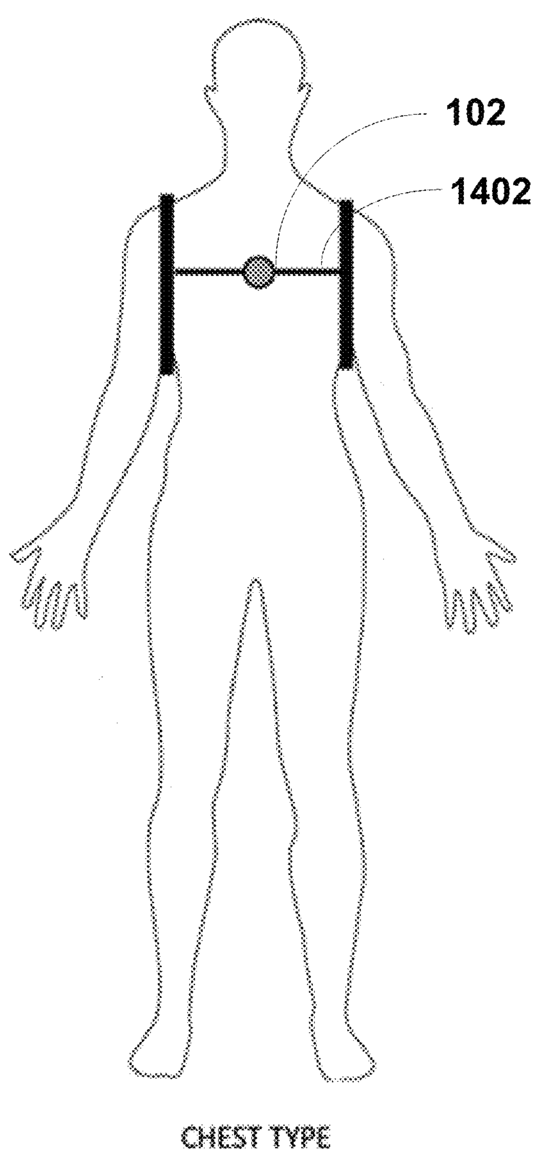
FIG. 14. illustrates an example of the sensor located on a chest of a subject.

FIG. 14 illustrates an example of the sensor located on a chest of a subject. For example, a band 1402 may partially or completely wrap around a chest of the subject. As the subject breaths in or out the band may expand or contract, changing the pressure on the sensor.

Figure 15:
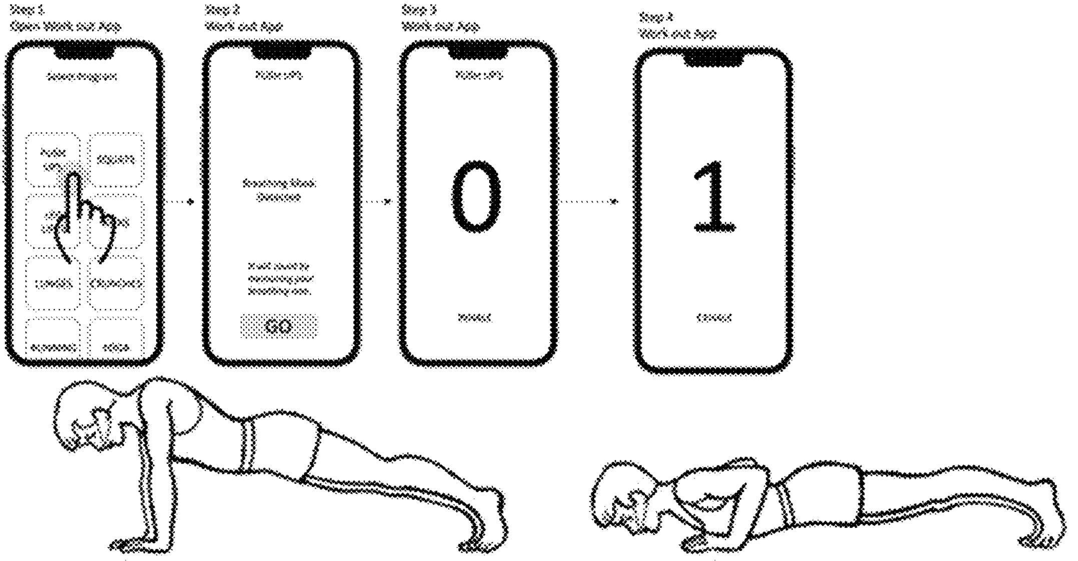
FIG. 15 illustrates examples of a user interface for a system.

FIG. 15 illustrates examples of a user interface for the system. The wearable device may be in communication with an external device, such as a mobile phone. The external device may display indications of physiological events, such as inhalation and exhalation as shown in FIG. 15. In some examples, the device may output the physiological event (i.e. inhalation or exhalation), and the external device may calculate additional physiological measurements, such as respiration rate.

Figure 16:
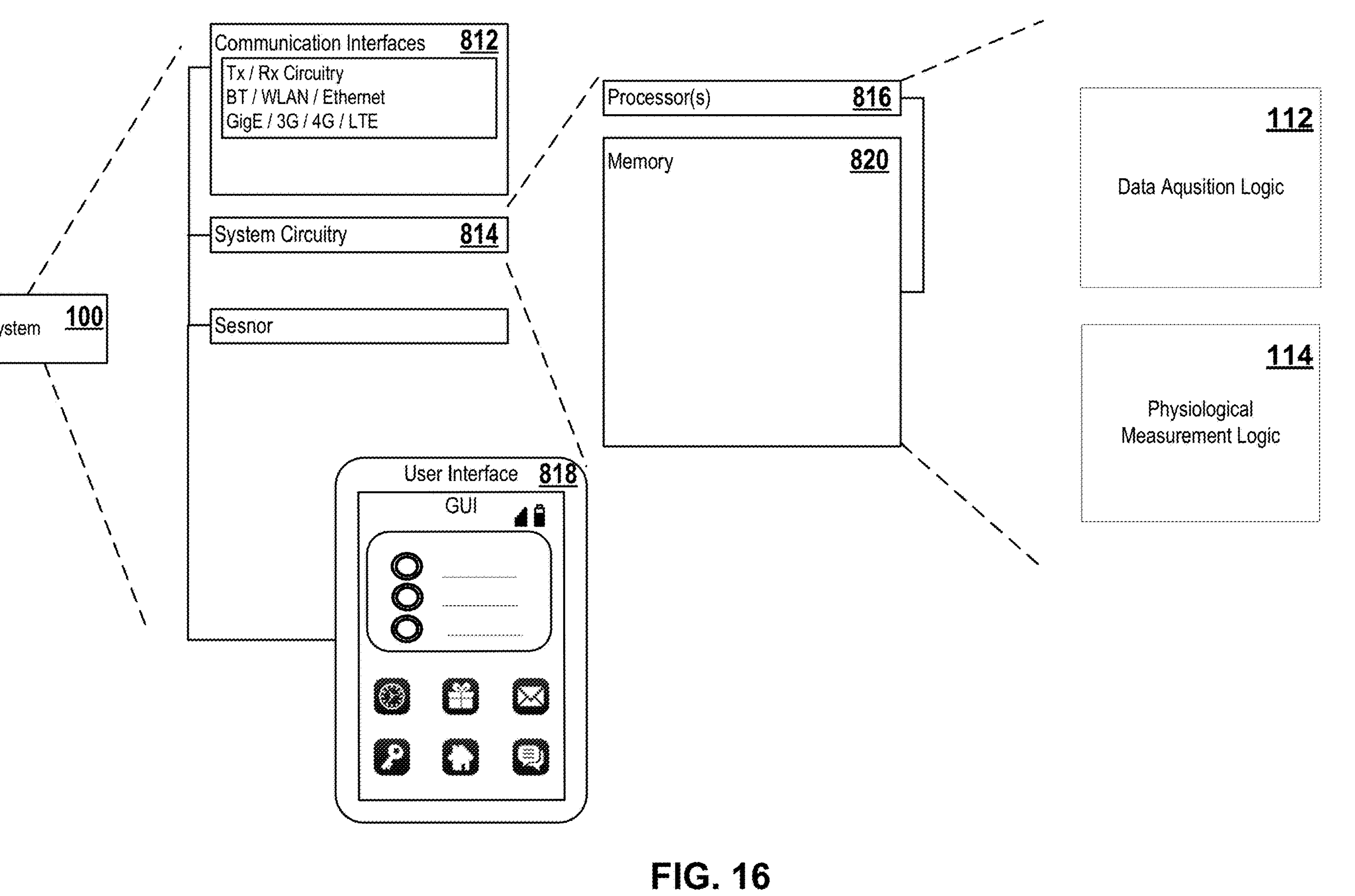
FIG. 16 illustrates a second example of a system.

FIG. 16 illustrates a second example of a system 100. The system 100 may include communication interfaces 812, the sensor 102 and/or system circuitry 814. The system circuitry 814 may include a processor 816 or multiple processors. Alternatively or in addition, the system circuitry 814 may include memory 820.

The processor 816 may be in communication with the memory 820. In some examples, the processor 816 may also be in communication with additional elements, such as the communication interfaces 812, the input interfaces 828, and/or the user interface 818. Examples of the processor 816 may include a general processor, a central processing unit, logical CPUs/arrays, a microcontroller, a server, an application specific integrated circuit (ASIC), a digital signal processor, a field programmable gate array (FPGA), and/or a digital circuit, analog circuit, or some combination thereof.

The processor 816 may be one or more devices operable to execute logic. The logic may include computer executable instructions or computer code stored in the memory 820 or in other memory that when executed by the processor 816, cause the processor 816 to perform the operations the data acquisition logic, the physiological measurement logic, and/or the system 100. The computer code may include instructions executable with the processor 816.

The memory 820 may be any device for storing and retrieving data or any combination thereof. The memory 820 may include non-volatile and/or volatile memory, such as a random access memory (RAM), a read-only memory (ROM), an erasable programmable read-only memory (EPROM), or flash memory. Alternatively or in addition, the memory 820 may include an optical, magnetic (hard-drive), solid-state drive or any other form of data storage device. The memory 820 may include at least one of the data acquisition logic, the physiological measurement logic, and/or the system 100. Alternatively or in addition, the memory may include any other component or sub-component of the system 100 described herein.

The user interface 818 may include any interface for displaying graphical information. The system circuitry 814 and/or the communications interface(s) 812 may communicate signals or commands to the user interface 818 that cause the user interface to display graphical information. Alternatively or in addition, the user interface 818 may be remote to the system 100 and the system circuitry 814 and/or communication interface(s) may communicate instructions, such as HTML, to the user interface to cause the user interface to display, compile, and/or render information content. In some examples, the content displayed by the user interface 818 may be interactive or responsive to user input. For example, the user interface 818 may communicate signals, messages, and/or information back to the communications interface 812 or system circuitry 814.

The system 100 may be implemented in many different ways. In some examples, the system 100 may be implemented with one or more logical components. For example, the logical components of the system 100 may be hardware or a combination of hardware and software. The logical components may include the data acquisition logic, the physiological measurement logic, or any component or subcomponent of the system 100. In some examples, each logic component may include an application specific integrated circuit (ASIC), a Field Programmable Gate Array (FPGA), a digital logic circuit, an analog circuit, a combination of discrete circuits, gates, or any other type of hardware or combination thereof. Alternatively or in addition, each component may include memory hardware, such as a portion of the memory 820, for example, that comprises instructions executable with the processor 816 or other processor to implement one or more of the features of the logical components. When any one of the logical components includes the portion of the memory that comprises instructions executable with the processor 816, the component may or may not include the processor 816. In some examples, each logical component may just be the portion of the memory 820 or other physical memory that comprises instructions executable with the processor 816, or other processor(s), to implement the features of the corresponding component without the component including any other hardware. Because each component includes at least some hardware even when the included hardware comprises software, each component may be interchangeably referred to as a hardware component.

Some features are shown stored in a computer readable storage medium (for example, as logic implemented as computer executable instructions or as data structures in memory). All or part of the system and its logic and data structures may be stored on, distributed across, or read from one or more types of computer readable storage media. Examples of the computer readable storage medium may include a hard disk, a floppy disk, a CD-ROM, a flash drive, a cache, volatile memory, non-volatile memory, RAM, flash memory, or any other type of computer readable storage medium or storage media. The computer readable storage medium may include any type of non-transitory computer readable medium, such as a CD-ROM, a volatile memory, a non-volatile memory, ROM, RAM, or any other suitable storage device.

The processing capability of the system may be distributed among multiple entities, such as among multiple processors and memories, optionally including multiple distributed processing systems. Parameters, databases, and other data structures may be separately stored and managed, may be incorporated into a single memory or database, may be logically and physically organized in many different ways, and may implemented with different types of data structures such as linked lists, hash tables, or implicit storage mechanisms. Logic, such as programs or circuitry, may be combined or split among multiple programs, distributed across several memories and processors, and may be implemented in a library, such as a shared library (for example, a dynamic link library (DLL).

All of the discussion, regardless of the particular implementation described, is illustrative in nature, rather than limiting. For example, although selected aspects, features, or components of the implementations are depicted as being stored in memory(s), all or part of the system or systems may be stored on, distributed across, or read from other computer readable storage media, for example, secondary storage devices such as hard disks, flash memory drives, floppy disks, and CD-ROMs. Moreover, the various logical units, circuitry and screen display functionality is but one example of such functionality and any other configurations encompassing similar functionality are possible.

The respective logic, software or instructions for implementing the processes, methods and/or techniques discussed above may be provided on computer readable storage media. The functions, acts or tasks illustrated in the figures or described herein may be executed in response to one or more sets of logic or instructions stored in or on computer readable media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one example, the instructions are stored on a removable media device for reading by local or remote systems. In other examples, the logic or instructions are stored in a remote location for transfer through a computer network or over telephone lines. In yet other examples, the logic or instructions are stored within a given computer and/or central processing unit ("CPU").

Furthermore, although specific components are described above, methods, systems, and articles of manufacture described herein may include additional, fewer, or different components. For example, a processor may be implemented as a microprocessor, microcontroller, application specific integrated circuit (ASIC), discrete logic, or a combination of other type of circuits or logic. Similarly, memories may be DRAM, SRAM, Flash or any other type of memory. Flags, data, databases, tables, entities, and other data structures may be separately stored and managed, may be incorporated into a single memory or database, may be distributed, or may be logically and physically organized in many different ways. The components may operate independently or be part of a same apparatus executing a same program or different programs. The components may be resident on separate hardware, such as separate removable circuit boards, or share common hardware, such as a same memory and processor for implementing instructions from the memory. Programs may be parts of a single program, separate programs, or distributed across several memories and processors.

A second action may be said to be "in response to" a first action independent of whether the second action results directly or indirectly from the first action. The second action may occur at a substantially later time than the first action and still be in response to the first action. Similarly, the second action may be said to be in response to the first action even if intervening actions take place between the first action and the second action, and even if one or more of the intervening actions directly cause the second action to be performed. For example, a second action may be in response to a first action if the first action sets a flag and a third action later initiates the second action whenever the flag is set.

To clarify the use of and to hereby provide notice to the public, the phrases "at least one of <A>, <B>, . . . and <N>" or "at least one of <A>, <B>, <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed.

While various embodiments have been described, it will be apparent to those of ordinary skill in the art that many more embodiments and implementations are possible. Accordingly, the embodiments described herein are examples, not the only possible embodiments and implementations.

What is claimed is:

1. A wearable device comprising:

a sensor comprising, a flexible fabric;

a poly(3,4-ethylenedioxythiophene) (PEDOT) coating conformally deposited on the fabric via vapor-phase oxidative chemical vapor deposition (oCVD) wherein deformation of the fabric causes a resistance change in the PEDOT coating, and a plurality of electrodes coupled to the PEDOT coating; and a processor communicatively coupled to the electrodes, the processor configured to:

measure an electrical property across the electrodes; and determine a physiological event based on the measured electrical property caused by the deformation of the fabric and the resistance change of the PEDOT coating; and output measurement information corresponding to the physiological event.

2. The wearable device of claim 1, wherein flexible fabric is foldable to substantially 180 degrees.

3. The wearable device of claim 1, wherein the physiological event includes inhalation exhalation, or a combination thereof.

4. The wearable device of claim 3, wherein the measurement information comprises a respiration rate.

5. The wearable device of claim 1, wherein the physiological event includes a pulse.

6. The wearable device of claim 5, wherein the measurement information comprises a blood pressure.

7. The wearable device of claim 1, further comprising conductive wires connected to the fabric and a housing with the processor disposed therein.

8. The wearable device of claim 1, further comprising a band connected to the fabric, the band configured to wrap around a body of a subject and stretch the fabric in response to respiration by the subject.

9. The wearable device of claim 1, further comprising a power source configured to cause a voltage across the electrodes.

10. The wearable device of claim 1, wherein the electrical property is current, resistance, conductivity, or a combination thereof.

11. A wearable article, comprising:

a sensor comprising, a flexible fabric;

a poly(3,4-ethylenedioxythiophene) (PEDOT) coating conformally deposited on the fabric via vapor-phase oxidative chemical vapor deposition (oCVD) such that deformation of the fabric causes a resistance change in the coating, and a plurality of electrodes coupled to the conjugated polymer coating.

12. The wearable article of claim 11, wherein the wearable article is configured to be worn by a hand.

13. The wearable article of claim 12, wherein the wearable article comprises a glove.

14. The wearable article of claim 11, wherein the wearable article is a facemask and the flexible fabric is included on the facemask, wherein deformations of the facemask during breathing cause the change in resistance across the polymer coating on the fabric.

15. The wearable device of claim 14, wherein the fabric is a strip configured to be place in front of the nostrils of a subject while leaving a mouth of the subject unobstructed.

* * * * *